United States Patent [19]

Foxton et al.

[11] 4,074,047

[45] Feb. 14, 1978

[54] 7[2-(AMINOCARBONYLALKOX-YIMINO)ACETAMIDO] DERIVATIVES OF CEPHALOSPORIN

[75] Inventors: Michael W. Foxton, Chalfont, St. Giles; Gordon I. Gregory, Chalfont, St. Peter; David M. Rogers, Ulverston, all of England

[73] Assignee: Glaxo Laboratories Limited, Greenford, England

[21] Appl. No.: 694,465

[22] Filed: June 9, 1976

[30] Foreign Application Priority Data

June 19, 1975 United Kingdom ............... 26188/75

[51] Int. Cl.² .................. C07D 501/32; C07D 501/34
[52] U.S. Cl. ..................................... 544/30; 424/246; 544/24; 544/25; 544/26; 544/27; 544/29; 260/347.3; 560/35
[58] Field of Search ..................................... 260/243 C

[56] References Cited

U.S. PATENT DOCUMENTS 3,971,778  7/1976  Cook et al. ....................... 260/243 C

FOREIGN PATENT DOCUMENTS 2,460,537  7/1975  Germany ......................... 260/243 C
2,204,060  8/1972  Germany ......................... 260/243 C
2,223,375  11/1972  Germany ......................... 260/243 C
2,262,500  7/1973  Germany.

OTHER PUBLICATIONS

Morrison et al., Organic Chemistry, 1966, p. 659.
Flynn–Cephalosporins and Penicillins, pp. 562, 563, (1973).

*Primary Examiner*—Nicholas S. Rizzo
*Assistant Examiner*—David E. Wheeler
*Attorney, Agent, or Firm*—Bacon & Thomas

[57] ABSTRACT

Cephalosporin antibiotics in which the 7β-acylamido group has the structure

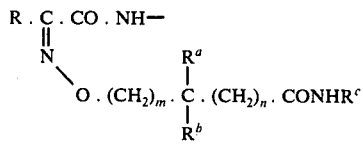

(where R is phenyl, thienyl or furyl; $R^a$ and $R^b$ are each selected from hydrogen, $C_{1-4}$ alkyl, $C_{2-4}$ alkenyl, $C_{3-7}$ cycloalkyl, phenyl, naphthyl, thienyl, furyl, carboxy, $C_{2-5}$ alkoxycarbonyl, aminocarbonyl, N-substituted aminocarbonyl and cyano, or $R^a$ and $R^b$ together with the carbon atom to which they are attached form a $C_{3-7}$ cycloalkylidene or cycloalkenylidene group; $R^c$ is hydrogen or $C_{1-4}$ alkyl; and $m$ and $n$ are each 0 or 1 such that the sum of $m$ and $n$ is 0 or 1) exhibit broad spectrum antibiotic activity characterized by particularly high activity against gram negative microorganisms, including those which produce β-lactamases. The compounds, which are syn isomers or exist as mixtures of syn and anti isomers containing at least 90% of the syn isomer, have particularly good activity against Proteus organisms including indole positive strains and, especially when both $R^a$ and $R^b$ are other than hydrogen, against Pseudomonas organisms.

6 Claims, No Drawings

7[2-(AMINOCARBONYLALKOX-YIMINO)ACETAMIDO] DERIVATIVES OF CEPHALOSPORIN

This invention is concerned with improvements in or relating to cephalosporin compounds, and is more particularly concerned with a novel class of cephalosporin compounds possessing valuable antibiotic properties.

The cephalosporin compounds in this specification are named with reference to "cepham" after *J. Amer. Chem. Soc.*, 1962, 84, 3400, the term "cephem" referring to the basic cepham structure with one double bond.

Cephalosporin antibiotics are widely used in the treatment of diseases caused by pathogenic bacteria in human beings and animals, and are especially useful in the treatment of diseases caused by bacteria which are resistant to other antibiotics such as penicillin compounds, and in the treatment of penicillin-sensitive patients. In many instances it is desirable to employ a cephalosporin antibiotic which exhibits activity against both gram positive and gram negative microorganisms, and a significant amount of research has been directed to the development of various types of broad spectrum cephalosporin antibiotics.

Considerable interest is currently being directed to the development of broad spectrum cephalosporin antibiotics which possess high activity against gram negative organisms. Existing commercially available $\beta$-lactam antibiotics tend to exhibit comparatively low activity against certain gram negative organisms, e.g. indole positive Proteus organisms, which are an increasingly common source of infection in humans; such antibiotics are in general also substantially inactive against Pseudomonas organisms. Several Pseudomonas organisms are resistant to the majority of existing commercially available antibiotic compounds, and the practical therapeutic applications of aminoglycoside antibiotics such as gentamicin which do exhibit Pseudomonas activity tend to be limited or complicated by the high toxicity of these antibiotics. It is well known that cephalosporin antibiotics normally exhibit low toxicity in man, so that the development of broad spectrum cephalosporin antibiotics possessing high activity against gram negative organisms such as strains of indole positive Proteus and Pseudomonas fulfils a significant need in chemotherapy.

The present invention provides 7$\beta$-acylamidoceph-3-em-4-carboxylic acid antibiotics and non-toxic derivatives thereof which are characterised in that the said acylamido moiety has the formula

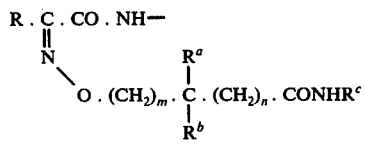

[wherein R is a phenyl, thienyl or furyl group; $R^a$ and $R^b$, which may be the same or different, are each selected from hydrogen, $C_{1-4}$ alkyl (e.g. methyl, ethyl, n-propyl, isopropyl or butyl), $C_{2-4}$ alkenyl (e.g. vinyl or allyl), $C_{3-7}$ cycloalkyl (e.g. cyclopropyl, cyclobutyl, cyclopentyl or cyclohexyl), phenyl, naphthyl, thienyl, furyl, carboxy, $C_{2-5}$ alkoxycarbonyl (e.g. ethoxycarbonyl), aminocarbonyl, N-substituted aminocarbonyl [e.g. N-($C_{1-4}$ alkyl)aminocarbonyl such as N-methylaminocarbonyl] and cyano, or $R^a$ and $R^b$ together with the carbon atom to which they are attached form a $C_{3-7}$ cycloalkylidene or cycloalkenylidene group (e.g. a cyclobutylidene, cyclopentylidene or cyclohexylidene group); $R^c$ is hydrogen or $C_{1-4}$ alkyl (e.g. a methyl, ethyl, propyl, isopropyl or t-butyl group) and m and m are each 0 or 1 such that the sum of m and n is 0 or 1], the compounds being syn isomers or existing as mixtures of syn and anti isomers containing at least 90% of the syn isomer.

These compounds, especially when $R^c$ is hydrogen, exhibit broad spectrum antibiotic activity. The compounds exhibit activity against microorganisms which produce $\beta$-lactamases, and also possess very high stability to $\beta$-lactamases produced by a range of gram negative organisms.

Compounds according to the invention have been found to exhibit good activity against various Proteus organisms (e.g. strains of *Proteus morganii* and *Proteus mirabilis*) and, especially when both $R^a$ and $R^b$ are other than hydrogen, against strains of *Pseudomonas aeruginosa*.

The compounds of the invention are defined as having the syn isomeric form as regards the configuration of the group

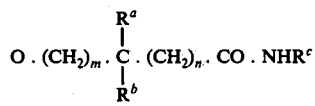

with respect to the carboxamido group. In this specification the syn configuration is denoted structurally as

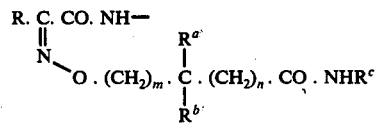

this configuration being assigned on the basis of the work of Ahmad and Spenser reported in *Can. J. Chem.*, 1961, 39, 1340. As indicated above, the compounds may exist as mixtures of syn and anti isomers provided that such mixtures contain at least 90% of the syn isomer. We prefer, however, the compounds to be syn isomers essentially free from the corresponding anti isomer.

The antibiotic compounds of the invention therefore comprise compounds of the general formula:

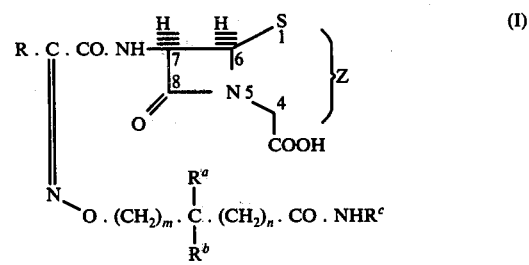

(wherein R, $R^a, R^b, R^c$, m and n have the above-defined meanings and Z is a group in which 2 carbon atoms link the nuclear sulphur atom and the 4-position carbon atom such that the compound possesses $\Delta^3$ olefinic unsaturation) and non-toxic derivatives thereof.

By "non-toxic derivatives" is meant those derivatives which are physiologically acceptable in the dosage at which they are administered. Such derivatives may include, for example, salts, biologically acceptable esters, 1-oxides and solvates (especially hydrates). It will be appreciated that where $R^a$ or $R^b$ is carboxy, derivatives such as salts and esters may be formed by reaction of either or both of the carboxy groups present in such compounds of formula I.

Non-toxic salt derivatives which may be formed from the compounds of general formula I include inorganic base salts such as alkali metal salts (e.g. sodium and potassium salts) and alkaline earth metal salts (e.g. calcium salts); organic base salts (e.g. procaine, phenylethylbenzylamine, dibenzylethylenediamine, ethanolamine, diethanolamine, triethanolamine and N-methylglucosamine salts); and, where appropriate, acid addition salts, e.g. with hydrochloric, hydrobromic, sulphuric, nitric, phosphoric, trifluoroacetic, toluene-p-sulphonic and methane sulphonic acids. The salts may also be in the form of resinates formed with, for example, a polystyrene resin or cross-linked polystyrene divinylbenzene copolymer resin containing amino or quaternary amino groups, or, where appropriate, sulphonic acid groups, or, again where appropriate, with a resin containing carboxyl groups, e.g. a polyacrylic acid resin. Use of highly soluble base salts (e.g. alkali metal salts such as the sodium salt) of compounds of formula I is generally advantageous in therapeutic applications because of the rapid distribution of such salts in the body upon administration. Where, however, insoluble salts of compounds (I) are desired in a particular application, e.g. for use in depot preparations, such salts may be formed in conventional manner, for example with appropriate organic amines.

Biologically acceptable, metabolically labile ester derivatives which may be formed from compounds of formula I include, for example, acyloxymethyl esters, e.g. lower alkanoyloxymethyl esters such as acetoxymethyl or pivaloyloxymethyl esters.

It will be appreciated that when $R^a$ and $R^b$ in the above formulae are different, the carbon atom to which they are attached may comprise a centre of asymmetry; compounds in accordance with the invention wherein $R^a$ and $R^b$ are different may thus be diastereoisomeric. The invention embraces the individual diastereoisomers of such compounds as well as mixtures thereof.

The cephalosporin antibiotics according to the present invention may be unsubstituted at the 3-position or may carry at this position any of the wide range of substituents disclosed in the literature pertaining to cephalosporin compounds, the characterising feature of the invention being the nature of the 7β-acylamido group. The invention thus includes within its scope compounds of the general formula:

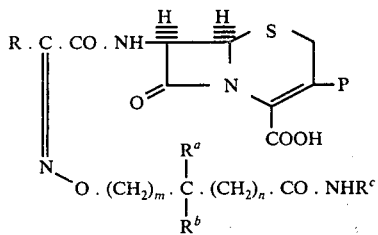

(II)

[where R,$R^a$,$R^b$, $R^c$, m and n are as hereinbefore defined and P represents a hydrogen atom; a halogen atom such as fluorine, chlorine or bromine; or an organic group, for example a saturated or unsaturated, substituted or unsubstituted, organic group containing 1–20 carbon atoms] and non-toxic derivatives thereof.

Where P is an unsaturated organic group it may, for example, be a group of the formula

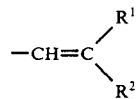

wherein $R^1$ and $R^2$, which may be the same or different, are each selected from hydrogen, carboxy, cyano, $C_{2-7}$ alkoxycarbonyl (e.g. methoxycarbonyl or ethoxycarbonyl), and substituted or unsubstituted aliphatic (e.g. alkyl, preferably $C_1$-$C_6$ alkyl such as methyl, ethyl, iso-propyl or n-propyl), $C_5$-$C_7$ cycloaliphatic (e.g. $C_{5-7}$ cycloalkyl such as cyclopentyl or cyclohexyl), $C_7$-$C_{10}$ araliphatic (e.g. phenyl $C_{1-4}$ alkyl such as benzyl or phenylethyl) and $C_6$-$C_{12}$ aromatic (e.g. mono- or bicyclic carbocyclic aryl such as phenyl, nitrophenyl, tolyl or naphthyl) groups. Specific substituted vinyl groups of the above formula include 2-carboxyvinyl, 2-methoxycarbonylvinyl, 2-ethoxycarbonylvinyl and 2-cyanovinyl.

P may also be an unsubstituted or substituted methyl group, which may be depicted by the formula

—CH$_2$Y where Y is a hydrogen atom or a nucleophilic atom or group, e.g. the residue of a nucleophile or a derivative of a residue of a nucleophile. Y may thus, for example, be derived from the wide range of nucleophilic substances characterised by possessing a nucleophilic nitrogen, carbon, sulphur or oxygen atom described widely in earlier patents and literature pertaining to cephalosporin chemistry. Examples of such nucleophiles include:

NITROGEN NUCLEOPHILES

Examples of nitrogen nucleophiles include tertiary aliphatic, aromatic, araliphatic and cyclic amines, for example tri($C_{1-6}$ alkyl) amines such as triethylamine, and heterocyclic tertiary amines. The heterocyclic tertiary amines may if desired contain one or more further heteroatoms in addition to the basic nitrogen atom, and may be substituted or unsubstituted. The heterocyclic tertiary amine may thus, for example, be a pyridine, pyrimidine, pyridazine, pyrazine, pyrazole, imidazole, triazole or thiazole; a fused bi- or poly-cyclic analogue of any of these heterocycles, for example purine or benzotriazole; and any of the above amines substituted by one or more aliphatic (e.g. lower alkyl such as methyl, ethyl, n-propyl or isopropyl), aryl (e.g. $C_{6-12}$ mono- or bicyclic carbocyclic aryl such as phenyl or naphthyl), araliphatic (e.g. phenyl lower alkyl such as benzyl or phenylethyl), lower alkoxymethyl (e.g. methoxymethyl, ethoxymethyl, n-propoxymethyl or iso-propoxymethyl), acyloxymethyl (e.g. lower alkanoyloxymethyl such as acetoxymethyl), formyl, acyloxy (e.g. lower alkanoyloxy such as acetoxy), carboxy, esterified carboxy (e.g. lower alkoxycarbonyl such as methoxycarbonyl), carboxy lower alkyl (e.g. carboxymethyl), sulpho, lower alkoxy (e.g. methoxy, ethoxy, n-propoxy or iso-propoxy), aryloxy (e.g. phenoxy), aralkoxy (e.g. benzyloxy), alkylthio (e.g. methylthio or ethylthio), arylthio, aralkylthio, cyano, hydroxy, carbamoyl, N-monoloweralkylcarbamoyl (e.g.

N-methylcarbamoyl or N-ethylcarbamoyl), N,N-diloweralkylcarbamoyl (e.g. N,N-dimethylcarbamoyl or N,N-diethylcarbamoyl), N-(hydroxyloweralkyl)carbamoyl (e.g. N(hydroxymethyl)carbamoyl or N-(hydroxyethyl)carbamoyl), or carbamoylloweralkyl (e.g. carbamoylmethyl or carbamoylethyl) groups. Examples of Y groups which may be obtained from heterocyclic tertiary amine nucleophiles of the above type include pyridinium, 3- and 4-carbamoylpyridinium, 3-carboxymethylpyridinium, 3-sulphopyridinium, thiazol-3-yl, pyrazol-1-yl, pyridazinium, and benzotriazol-1yl.

Another class of nitrogen nucleophiles comprises azides, e.g. alkali metal azides such as sodium azide.

When the group Y is a derivative of a residue of a nitrogen nucleophile it may be, for example, an amino group or an acylamido group. Compounds in which Y is amino may be derived from the corresponding compound in which Y is azido by reduction, e.g. by catalytic hydrogenation of the azide using a precious metal catalyst such as palladium or platinum. Compounds in which Y is an acylamido group may be derived by acylation of a compound wherein Y is amino, e.g. by any method suitable for acylating an aminocephalosporin, for example reaction of the amino compound with an acid chloride, acid anhydride or mixed anhydride of an acid corresponding to the desired acyl group and another acid.

Compounds wherein Y is amino may also be reacted with a substituted isocyanate or isothiocyanate to yield urea or thiourea derivatives.

Other compounds in which Y is a derivative of a residue of a nitrogen nucleophile may be obtained by reacting a compound in which Y is azido with a dipolarophile. Examples of suitable dipolarophiles include acetylenic, ethylenic and cyano dipolarophiles.

Acetylenic dipolarophiles may be shown as having the structure

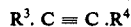

wherein $R^3$ and $R^4$, which may be the same or different, are atoms or groups.

In general we prefer that $R^3$ and preferably also $R^4$ should be of an electronegative nature. Examples of such groups include cyano, $CO_2R^5$, $COR^5$ (where $R^5$ is, for example, hydrogen, lower alkyl, aryl or lower aralkyl), and trihalomethyl e.g. trifluoromethyl.

However, $R^3$ and preferably also $R^4$ could be electropositive e.g. alkoxy or alkylamino.

$R^3$ and $R^4$ may together form a ring system with the acetylenic group such as, for example, in an aryne.

Where $R^3$ and $R^4$ are discrete atoms or groups which are identical a single compound will result on reaction with the azido cephalosporin; if they are different one will in general obtain a mixture of position isomers.

Ethylenic dipolarophiles may be shown as having the structure

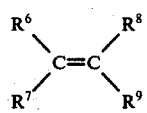

where $R^6$, $R^7$, $R^8$ and $R^9$ which may be the same or different are atoms or groups. Although $R^6$, $R^7$, $R^8$ and $R^9$ may all be hydrogen, ethylene per se, like acetylene, reacts sluggishly with azido groups. $R^6$ and $R^8$ may together form a cyclic structure, e.g. a carbocyclic structure, with the ethenoid group such that the double bond is strained. Examples of ethylenic dipolarophiles containing strained double bonds include norbornenes, transcycloalkenes and acenaphthalene.

Further ethylenic dipolarophiles which may be used include compounds of the formula $R^6.R^7C = CR^8.R^9$ where at least one of $R^6$, $R^7$, $R^8$ and $R^9$ is an electronegative group. $R^6$ and $R^8$ may thus be identical electronegative groups, $R^7$ and $R^9$ being other groups as desired. $R^7$ and $R^9$ may thus together form a ring system. Examples of such dipolarophiles include benzoquinone and nuclear substituted benzoquinones and maleimide. Again all of $R^6$, $R^7$, $R^8$ and $R^9$ may be identical electronegative groups. Electronegative groups which may be used include those listed under the section on acetylenic dipolarophiles and examples of such compounds thus include dicyanoethylene and lower mono- and di-alkoxycarbonyl ethylenes.

One or more of $R^6$, $R^7$, $R^8$ and $R^9$ may if desired by electropostive.

Cyano compounds, especially those which are activated by electronegative groups, may function as cyano dipolarophiles. Examples of such dipolarophiles include lower alkoxycarbonyl cyanides and cyanogen.

CARBON NUCLEOPHILES

Examples of carbon nucleophiles include inorganic cyanides, pyrroles and substituted pyrroles, e.g. indoles, and compounds giving stabilised carbanions, for example acetylenes and compounds having $\beta$-diketone groups, for example acetoacetic and malonic esters and cyclohexane-1,3-diones or enamines, ynamines or enols.

The carbon nucleophile may thus give rise to cephalosporin compounds characterized by possessing a substituent at the 3-position in which a carbonyl group is linked to the cephalosporin nucleus through two carbon atoms. Such compounds may thus possess as the 3-substituent a group of the formula

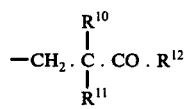

wherein $R^{10}$ and $R^{11}$, which may be the same or different, are selected from hydrogen; cyano; lower alkyl e.g. methyl or ethyl; phenyl; phenyl substituted by, for example, halo, lower alkyl, lower alkoxy, nitro, amino or lower alkylamino; carboxy; lower alkoxycarbonyl; mono- or di-aryl lower alkoxycarbonyl; lower alkylcarbonyl; aryl lower alkyl or $C_5$ or $C_6$ cycloalkyl and $R^{12}$ is selected from hydrogen; lower alkyl e.g. methyl or ethyl; phenyl; phenyl substituted by, for example, halo, lower alkyl, lower alkoxy, nitro, amino or lower alkylamino; aryl lower alkyl or $C_5$ or $C_6$ cycloalkyl.

SULPHUR NUCLEOPHILES

Examples of sulphur nucleophiles include thioureas, including aliphatic, aromatic, araliphatic, alicyclic and heterocyclic substituted thioureas; dithiocarbamates; aromatic, aliphatic and cyclic thioamides, for example thioacetamide and thiosemicarbazide; thiosulphates; thiols; thiophenols; thioacids, e.g. thiobenzoic acid or thiopicolinic acid; and dithioacids.

One class of sulphur nucleophile includes those compounds of the formula: $R^{13}.S(O)_nH$ in which $R^{13}$ is an aliphatic e.g. lower alkyl such as methyl, ethyl or n-propyl group; an alicyclic e.g. lower cycloalkyl such as cyclohexyl or cyclopentyl group; an aromatic e.g. $C_{6-12}$ mono- or bicyclic carboxylic aryl such as phenyl or naphthyl group; an araliphatic e.g. phenyl lower (e.g. $C_{1-4}$) alkyl such as benzyl group; or a heterocyclic group, and $n$ is 0, 1 or 2. A preferred class of nucleophiles falling within the above formula is that having the general formula $R^{14}SH$ in which $R^{14}$ is aliphatic, e.g. lower alkyl such as methyl, ethyl or n-propyl or lower alkanoyl such as acetyl; araliphatic, e.g. phenyl lower alkyl such as benzyl or phenethyl or substituted phenyl lower alkyl; alicyclic, e.g. cycloalkyl such as cyclopentyl or cyclohexyl; aromatic, e.g. phenyl, substituted phenyl or a heterocyclic group containing at least one 5- or 6-membered ring and having one or more heteroatoms selected from O, N and S. Such heterocyclic groups $R^{14}$ may be substituted, and examples of suitable heterocyclic groups include thiadiazolyl, e.g. 5-methyl-1,3,4-thiadiazol-2-yl; diazolyl; thiazolyl, e.g. triazol-4-yl; tetrazolyl, e.g. 1-methyltetrazol-5-yl, 1-ethyltetrazol-5-yl or 1-phenyltetrazol-5-yl; thiazolyl; thiatriazolyl; oxazolyl; oxadiazolyl, e.g. 2-phenyl-1,3,4-oxadiazol-5-yl; pyridyl, e.g. N-methylpyrid-2-yl; pyrimidyl; fused heterocyclic ring systems such as benzimidazolyl, benzoxazolyl, benzothiazolyl such as benzothiazol-2-yl, triazolopyridyl or purinyl; and substituted versions of such fused ring systems, e.g. nitrobenzothiazol-2-yl such as 5- or 6-nitrobenzothiazol-2-yl.

OXYGEN NUCLEOPHILES

Examples of oxygen nucleophiles include water; alcohols, for example alkanols such as methanol, ethanol, propanol and butanol; and lower alkanoic and alkenoic acids.

The term "oxygen nucleophile" thus includes compounds of the following formula:

$$R^{15}OH$$

in which the group $R^{15}$ may be lower alkyl (e.g. methyl, ethyl, n-propyl, isopropyl, n-butyl or isobutyl); lower alkenyl (e.g. allyl); lower alkynyl(e.g. propynyl); lower cycloalkyl (e.g. cyclopropyl, cyclopentyl or cyclohexyl); lower cycloalkyl lower alkyl (e.g. cyclopropylmethyl, cyclopentylmethyl or cyclohexylethyl); aryl (e.g. phenyl or naphthyl); aryl lower alkyl (e.g. benzyl); heterocyclic(e.g. a heterocyclic group as defined for $R^{14}$, such as N-methylpyrid-2-yl); heterocyclic lower alkyl (e.g. furfuryl); or any of these groups substituted by, for example, one or more of lower alkoxy (e.g. methoxy or ethoxy), lower alkylthio (e.g. methylthio or ethylthio), halogen (chlorine, bromine, iodine or fluorine), lower alkyl (e.g. methyl or ethyl), nitro, hydroxy, acyloxy, carboxy, carbalkoxy, lower alkylcarbonyl, lower alkylsulphonyl, lower alkoxysulphonyl, amino, lower alkylamino or acylamino groups.

In the case in which water is the nucleophile there will be obtained 3-hydroxymethyl cephalosporin compounds. Such 3-hydroxymethyl compounds and non-toxic derivatives thereof may show antibacterial activity and it is of note that they may be metabolites of compounds of general formula II where P is acetoxymethyl. 3-Hydroxymethyl cephalosporins may be acylated to form derivatives characterized by possessing the group 3-$CH_2$.O.CO.$R^{16}$ or 3—$CH_2$.O.CO.A$R^{17}$ where A is O, S or NH, $R^{16}$ is an organic group and $R^{17}$ is hydrogen or an organic group.

The group $R^{16}CO$ or $R^{17}A.CO$— may be chosen from among the wide class of such groups described in the literature and may have up to 20 carbon atoms. $R^{16}$ and, where appropriate, $R^{17}$ may thus each be a hydrocarbon group or such a group carrying one or more substituent atoms or groups, and may thus be chosen from the following list, which is not intended to be exhaustive: (i) $C_nH_{2n+1}$ where $n$ is an integer from 1 to 7, e.g. 1 to 4. The group may be straight or branched and, if desired, may be interrupted by an oxygen or sulphur atom or an imino group or substituted by cyano, carboxy, lower alkoxycarbonyl, hydroxy, carboxycarbonyl (HOOC.CO.), halogen (e.g. chlorine, bromine or iodine) or amino. Examples of such groups include methyl, ethyl, propyl, isopropyl, n-butyl, t-butyl, sec.-butyl and 2-chloroethyl.

(ii) $C_nH_{2n-1}$ where $n$ is an integer from 2 to 7. The group may be straight or branched and, if desired, may be interrupted by an oxygen or sulphur atom or an imino group. Examples of such groups include vinyl and propenyl.

(iii) $R^{18}$, where $R^{18}$ is carbocyclic aryl (e.g. $C_{6-12}$ mono- or bicyclic carbocyclic aryl), heterocyclic aryl (e.g. comprising a 5- or 6-membered ring containing at least one of O, N and S), lower cycloalkyl, substituted aryl and substituted cycloalkyl. Examples of this group include phenyl; substituted phenyl e.g. hydroxyphenyl, chlorophenyl, fluorophenyl, tolyl, nitrophenyl, aminophenyl, methoxyphenyl or methylthiophenyl; thien-2- and -3-yl; pyridyl; cyclohexyl; cyclopentyl; cyclopropyl; sydnone; naphthyl; and substituted naphthyl e.g. 2-ethoxynaphthyl.

(iv) $R^{18}$ $(CH_2)_m$ where $R^{18}$ has the meaning defined above under (iii) and $m$ is an integer from 1 to 4. Examples of this group include methyl, ethyl or butyl substituted by the various specific $R^{18}$ groups listed under (iii), e.g. lower cycloalkyl $C_{1-4}$ alkyl and carbocyclic or heterocyclic aryl $C_{1-4}$ alkyl such as benzyl and the appropriate substituted benzyl groups.

3-Position substituents of the above type thus include lower alkanoyloxymethyl groups such as acetoxymethyl and isobutyryloxymethyl, lower alkenoyloxymethyl groups such as crotonyloxymethyl; aroyloxymethyl groups such as benzoyloxymethyl; carbamoyloxymethyl, N-(lower alkyl)carbamoyloxymethyl such as N-methylcarbamoyloxymethyl, and N-(haloalkyl)carbamoyloxymethyl such as N-(2-chloroethyl)carbamoyloxymethyl.

A further important class of cephalosporin compounds are those possessing the group 3-$CH_2$Hal wherein Hal is chlorine, bromine or iodine. Such compounds may be primarily of value as intermediates of use in the preparation of active cephalosporin compounds by replacement of the halogen atom by a nucleophile e.g. a nitrogen-, oxygen- or sulphur-containing nucleophile as hereinbefore described.

The term "lower" as used in this specification and the accompanying claims to qualify aliphatic groups denotes, unless otherwise stated, that the said group may contain up to 6 carbon atoms. "Lower" as used to qualify cycloaliphatic groups indicated that the group may contain 3-7 (e.g. 5-7) carbon atoms.

One class of cephalosporin antibiotics in accordance with the invention comprises compounds of general formula

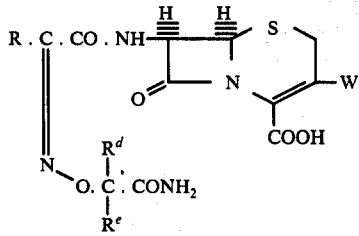 (III)

[wherein R is as hereinbefore defined; $R^d$ represents a methyl, ethyl, propyl, allyl or phenyl group and $R^e$ represents a hydrogen atom, a carboxy or aminocarbonyl group or a group as defined for $R^d$, or $R^d$ and $R^e$ together with the carbon atom to which they are attached form a cyclobutylidene, cyclopentylidene or cyclohexylidene group; and W is selected from:
(i) hydrogen,
(ii) acetoxymethyl,
(iii) benzoyloxymethyl,
(iv) carbamoyloxymethyl,
(v) N-methylcarbamoyloxymethyl,
(vi) a group of formula

(where $R^z$ represents cyano, carboxy or a $C_{2-5}$ alkoxycarbonyl group such as methoxycarbonyl or ethoxycarbonyl),
(vii) the group —CH$_2$G where G is the residue of a nitrogen nucleophile selected from compounds of the formula

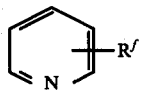

(wherein $R^f$ is hydrogen, carbamoyl, carboxymethyl or sulpho) and pyridazine, and
(viii) the group —CH$_2$SR$^w$ wherein $R^w$ is selected from pyridyl, diazolyl, triazolyl, tetrazolyl, thiazolyl, thiadiazolyl, oxadiazolyl, and substituted (e.g. lower alkyl- or phenyl-substituted) versions of these groups such as N-methylpyrid-2-yl, 1-methyltetrazol-5-yl, 1-phenyltetrazol-5-yl; 5-methyl-1,3,4-thiadiazol-2-yl and 5-phenyl-1,3,4-oxadiazol-2-yl] and non-toxic derivatives thereof.

The compounds according to the invention may be prepared by any convenient method, for example by techniques analagous to those described in Belgian Pat. No. 783449.

Thus according to one embodiment of the invention we provide a process for the preparation of an antibiotic compound of general formula I as hereinbefore defined or a non-toxic derivative thereof which comprises either (A) condensing a compound of the formula

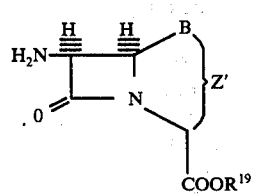 (IV)

[wherein B is >S or >S→O ($\alpha$- or $\beta$-); $R^{19}$ represents hydrogen or a carboxyl blocking group, e.g. the residue of an ester-forming aliphatic or araliphatic alcohol or an ester-forming phenol, silanol or stannanol (the said alcohol, phenol, silanol or stannanol preferably containing 1–20 carbon atoms) or a symmetrical or mixed anhydride group derived from an appropriate acid; and Z′ is a group in which 2 carbon atoms link the nuclear sulphur atom and the 4-position carbon atom so that the compound possesses $\Delta^2$ or $\Delta^3$ unsaturation] or a salt, e.g. an acid addition salt such as a hydrochloride, hydrobromide, sulphate, nitrate, phosphate, methane sulphonate or tosylate, or an N-silylated derivative thereof with an acid of formula

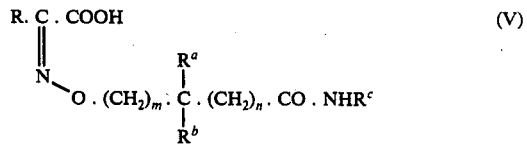 (V)

(wherein R, $R^a$, $R^b$, $R^c$, m and n are as hereinbefore defined) or with an acylating agent corresponding thereto; or (B), where Z in formula I is the group

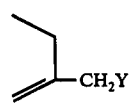

(where Y represents a nucleophilic atom or group) reacting a compound of the formula

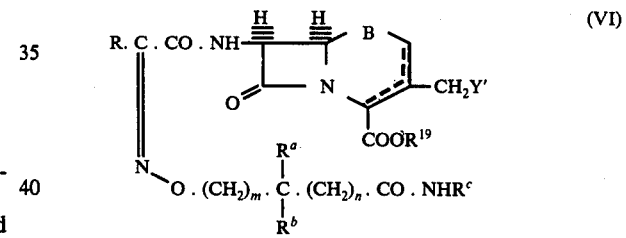 (VI)

(wherein B, R, $R^a$, $R^b$, $R^c$, $R^{19}$, m and n are as hereinbefore defined; Y′ is a replaceable residue of a nucleophile, e.g. an acetoxy or dichloroacetoxy group or a halogen atom such as chlorine, bromine or iodine; and the dotted line bridging the 2-, 3- and 4-positions indicates that the compound is a ceph-2-em or ceph-3-em compound) with a nucleophile; whereafter, if necessary and/or desired in each instance, any of the following reactions (C) in any appropriate sequence, are carried out:
(i) conversion of a $\Delta^2$ isomer into the desired $\Delta^3$ isomer,
(ii) reduction of a compound wherein B is >S→O to form a compound wherein B is >S,
(iii) reduction of a 3-azidomethyl compound to form a 3-aminomethyl compound,
(iv) acylation of a 3-aminomethyl compound to form a 3-acylaminomethyl compound,
(v) reaction of a 3-azidomethyl compound with a dipolarophile to form a compound having a polyazole ring linked to the 3-position carbon atom through a methylene group,
(vi) deacylation of a 3-acyloxymethyl compound to form a 3-hydroxymethyl compound,
(vii) acylation of a 3-hydroxymethyl compound to form a 3-acyloxymethyl compound, (viii) carbamoylation of a 3-hydroxymethyl compound to form an unsubstituted or substituted 3-carbamoyloxymethyl compound, and (ix) removal of carboxyl blocking groups;

and finally (D) recovering the desired compound of formula I or a non-toxic derivative thereof, if necessary after separation of isomers.

Non-toxic derivatives of the compounds of formula I may be formed in any convenient way, for example according to methods well known in the art. Thus, for example, base salts may be formed by reaction of the cephalosporin acid with sodium 2-ethylhexanoate or potassium 2-ethylhexanoate. Biologically acceptable ester derivatives may be formed using conventional esterifying agents. 1-Oxides may be formed by treatment of the corresponding cephalosporin sulphide with an appropriate oxidising agent, for example with a peracid such as metaperiodic acid, peracetic acid, monoperphthalic acid or m-chloroperbenzoic acid, or with t-butyl hypochlorite, this last reagent conveniently being employed in the presence of a weak base such as pyridine.

Acylating agents which may be employed in the preparation of compounds of formula I include acid halides, particularly acid chlorides or bromides. Such acylating agents may be prepared by reacting an acid (V) or a salt thereof with a halogenating agent e.g. phosphorus pentachloride, thionyl chloride or oxalyl chloride. Treatment of the sodium, potassium or triethylammonium salt of the acid (V) with oxalyl chloride is advantageous in that under these conditions isomerisation is minimal.

Acylations employing acid halides may be effected in aqueous and non-aqueous reaction media, conveniently at temperatures of from $-50°$ to $+50°$ C, preferably $-20°$ to $+30°$ C, if desired in the presence of an acid binding agent. Suitable reaction media include aqueous ketones such as aqueous acetone, esters such as ethyl acetate, halogenated hydrocarbons such as methylene chloride, amides such as dimethylacetamide, nitriles such as acetonitrile, or mixtures of two or more such solvents. Suitable acid binding agents include tertiary amines (e.g. triethylamine or dimethylaniline), inorganic bases (e.g. calcium carbonate or sodium bicarbonate), and oxiranes such as lower 1,2-alkylene oxides (e.g. ethylene oxide or propylene oxide) which bind hydrogen halide liberated in the acylation reaction.

Acids of formula V may themselves be used as acylating agents in the preparation of compounds of formula I. Acylations employing acids (V) are desirably conducted in the presence of a condensation agent, for example a carbodiimide such as N,N'-diethyl-, dipropyl- or diisopropylcarbodiimide, N,N'-dicyclohexylcarbodiimide or N-ethyl-N'-γ-dimethylaminopropylcarbodiimide; a carbonyl compound such as carbonyldiimidazole; or an isoxazolinium salt such as N-ethyl-5-phenylisoxazolinium perchlorate. Acylation reactions of this type are desirably effected in an anhydrous reaction medium, e.g. methylene chloride, dimethylformamide or acetonitrile.

Acylation may also be effected with other amide-forming derivatives of acids of formula V such as, for example, a symmetrical anhydride or a mixed anhydride (e.g. with pivalic acid or formed with a haloformate such as a lower alkylhaloformate). The mixed or symmetrical anhydride may be generated in situ; thus, for example, a mixed anhydride may be generated using N-ethoxycarbonyl-2-ethoxy-1,2-dihydroquinoline.

Mixed anhydrides may also be formed with phosphorus acids (for example phosphoric or phosphorous acids), sulphuric acid or aliphatic or aromatic sulphonic acids (for example p-toluene sulphonic acid).

It will be appreciated that in processes for the preparation of compounds of formula I wherein $R^a$ or $R^b$ represents carboxy it will in many instances be necessary to protect the carboxy group, for example by substitution with a carboxyl blocking group, e.g. a group as hereinbefore defined in connection with $R^{19}$.

Any transformations of substituents at the 3-position which may be necessary in the preparation of particular compounds of formula I may, for example, be effected by methods described in the literature.

Thus, for example, compounds substituted at the 3-position by a group

wherein Y represents an ether or thioether group or a halogen atom may be prepared as described in British Pat. Nos. 1,241,656; 1,241,657; 1,277,415 and 1,279,402. Compounds wherein Y is the residue of a nucleophile may also be prepared by the reaction of a 3-acetoxymethyl cephalosporin compound with a nucleophile, for example pyridine or other tertiary amine as described in British Pat. No. 912,541; a sulphur-linking, nitrogen-linking or inorganic nucleophile as described in British Pat. No. 1,012,943; a sulphur-linking nucleophile as described in British Pat. Nos. 1,059,562; 1,101,423 and 1,206,305; or a nitrogen-linking nucleophile as described in British Pat. Nos. 1,030,630; 1,082,943 and 1,082,962. Compounds in which Y is a derivative of a residue of a nucleophile, e.g. where Y is an amino or acylamido group derived from an azido group may be prepared as described in British Pat. Nos. 1,057,883 and 1,211,694, these patents further describing the reaction compounds in which Y is azido with a dipolarophile. Compounds wherein Y is the residue of a nucleophile may also be prepared by the reaction of a 3-halomethylcephalosporin with any of the nucleophiles disclosed in the above references, such a process being described in British Pat. No. 1,241,657, or by the reaction of a 3-halomethylcephalosporin sulphoxide with any of the nucleophiles disclosed in the above references, such a process being described in British Pat. No. 1,326,531. The contents of the above mentioned British Patents are herein incorporated for reference purposes.

Where a 3-halomethylcephalosporin sulphide or sulphoxide ester is reacted with a tertiary nitrogen nucleophile such as pyridine in accordance with the process of British Pat. Nos. 1,241,657 or 1,326,531, the reaction product will usually be obtained in the form of, for example, the corresponding 3-pyridiniummethyl halide. It has been observed that deesterification of compounds of this type by treatment with trifluoroacetic acid tends to promote isomerisation of the oxyimino moiety in the 7β-acylamido side chain; such isomerisation is clearly undesirable if a product containing at least 90% of the syn isomer is to be obtained without the need for a subsequent isomer separation stage.

It has also been observed, however, that the tendency to isomerisation may be substantially lessened if the 3-pyridiniummethyl halide is converted into the 3-pyridiniummethyl salt of a non-hydrohalic acid (e.g. trifluoroacetic, acetic, formic, sulphuric, nitric or phosphoric acid) prior to deesterification. Conversion of the halide salt into a non-hydrohalic acid salt is conveniently effected by means of anion exchange. This may be brought about by, for example, use of a suitable anion exchange resin, for example in the trifluoroacetate form. Where an anion exchange resin is employed, the 3-pyridiniummethyl halide may be run through a column of the resin prior to deesterification. It may be advantageous to employ an inert organic solvent system (i.e. one which does not have a harmful effect on the resin) to ensure adequate solubility for the cephalosporin compound; organic solvent systems which may be used include lower alkanols such as ethanol, ketones such as acetone, and nitriles such as acetonitrile. Compounds possessing a 3-substituent $$- CH_2Y$$

wherein Y is a hydroxy group may be prepared by the methods described in British Pat. No. 2,121,308 and Belgian Pat. No. 841,937.

Where Y is a halogen (i.e. chlorine, bromine or iodine) atom, ceph-3-em starting compounds may be prepared by halogenation of a 7β-acylamido-3-methyl-ceph-3-em-4-carboxylic acid ester 1β-oxide followed by reduction of the 1β-oxide group later in the sequence as described in British Pat. No. 1,326,531. The corresponding ceph-2em compounds may be prepared by the method of Dutch published Patent Application No. 6,902,013 by reaction of a 3-methylceph-2-em compound with N-bromosuccinimide to yield the corresponding 3-bromomethylceph-2-em compound.

Carbamoylation of 3-hydroxymethyl compounds may be effected by conventional methods. Thus, for example, a 3-hydroxymethyl cephalosporin may be reacted with an isocyanate of formula $R^f$. NCO (wherein $R^f$ represents a labile substituent group or an alkyl group) to give a compound containing a 3-position substituent having the formula — $CH_2O.CONHR^f$ (wherein $R^f$ has the above defined meaning). Where $R^f$ is a labile substituent this substituent may if desired subsequently be cleaved, e.g. by hydrolysis, to form a 3-carbamoyloxymethyl group. Labile groups $R^f$ which are readily cleavable upon subsequent treatment include chlorosulphonyl and bromosulphonyl; halogenated lower alkanoyl groups such as dichloroacetyl and trichloroacetyl; and halogenated lower alkoxycarbonyl groups such as 2,2,2-trichloroethoxycarbonyl. These labile $R^f$ groups may generally be cleaved by acid or base catalysed hydrolysis (e.g. by base catalysed hydrolysis using sodium bicarbonate).

Another carbamoylating agent of use in the carbamoylation of 3-hydroxymethyl cephalosporins is cyanic acid, which is conveniently generated in situ from, for example, an alkali metal cyanate such as sodium cyanate, the reaction being facilitated by the presence of an acid, e.g. a strong organic acid such as trifluoroacetic acid. Cyanic acid effectively corresponds to a compound of formula $R^f$.NCO wherein $R^f$ is hydrogen, and therefore converts 3-hydroxymethyl cephalosporin compounds directly to their 3-carbamoyloxymethyl analogues.

3-Hydroxymethyl cephalosporins for use in the above carbamoylation reactions may, for example, be prepared by the methods described in British Pat. No. 1,121,308 and Belgian Pat. Nos. 783,449 and 841,937.

Cephalosporin compounds possessing an acyloxymethyl group as 3-position substituent may, for example, be prepared from a cephalosporin compound having a $-CH_2X$ group (where X = OH or the residue of an acid H X which has a pKa of not more that 4.0, preferably not more than 3.5, as measured in water at 25° C) at the 3-position. X may thus, for example, represent chlorine, bromine, iodine, formyloxy, an acetoxy group having at least one electron-withdrawing substituent on the α-carbon atom, or a nuclear substituted benzoyloxy group (the nuclear substituent being of the electron withdrawing type as described in British Pat. No. 1,241,657), and the nucleophilic displacement reaction to form the desired 3-position acyloxymethyl may be carried out as described in our aforesaid British Pat. No. 1,241,657. Alternatively, where X is hydroxy, a 3-acyloxymethyl cephalosporin may be obtained by acylation analogous with that described in British Pat. No. 1,141,293, i.e. by aralkylating the 4-carboxy group, acylating the 3-hydroxymethyl group of the protected compound and subsequently removing the aralkyl group.

Compounds having a vinyl or substituted vinyl group at the 3-position may be obtained by the method described in Belgian Pat. No. 761,897.

$\Delta^2$-Cephalosporin ester derivatives obtained in accordance with the process of the invention may be converted into the corresponding $\Delta^3$ derivative by, for example, treatment of the $\Delta^2$ ester with a base.

A ceph-2-em reaction product may also be oxidised to yield the corresponding ceph-3-em 1-oxide, for example by reaction with a peracid as mentioned previously; the resulting sulphoxide may, if desired, subsequently be reduced as described hereinafter to yield the corresponding ceph-3-em sulphide.

Where a compound is obtained in which B is $>S \rightarrow O$ this may be converted to the corresponding sulphide by, for example, reduction of the corresponding acyloxysulphonium or alkyloxysulphonium salt prepared in situ by reaction with e.g. acetyl chloride in the case of an acetoxysulphonium salt, reduction being effected by, for example, sodium dithionite or by iodide ion as in a solution of potassium iodide in a water miscible solvent e.g. acetic acid, tetrahydrofuran, dioxan, dimethylformamide or dimethylacetamide. The reaction may be effected at a temperature of $-20°$ to $+50°$ C.

Where a compound of formula I is obtained as a mixture of isomers, the syn isomer may be obtained by, for example, conventional methods such as crystallisation or chromatography. Syn and anti isomers may be distinguished by appropriate techniques, e.g. by their ultraviolet spectra, by thin layer or paper chromatography or by their proton magnetic resonance spectra. Thus, for example, the p.m.r. spectra of DMSO-$d_6$ solutions of syn compounds of Formula I exhibit the doublet for the amide NH at a lower field than do similar solutions of the corresponding anti-isomers. These factors may be employed in monitoring reactions.

Starting materials of formula IV wherein Z' is the group

may, for example, be prepared by the methods of Belgian Pat. No. 774,480 and French Pat. No. 2,165,834. Starting materials of formula IV wherein Z' is a group of formula

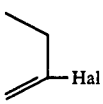

(where Hal represents a halogen atom such as fluorine, chlorine or bromine) may, for example, be prepared as described in German OLS No. 2,408,686.

Acids of formula (V) and acid halides and anhydrides corresponding thereto are novel and comprise a feature of the present invention.

For use as starting materials for the preparation of compounds of general formula I according to the invention, compounds of general formula V and acid halides and anhydrides corresponding thereto in their syn isomeric form or in the form of mixtures of the syn isomers and the corresponding anti isomers containing at least 90% of the syn isomer are preferably used.

Acids (V) may be prepared by etherification of an acid of formula

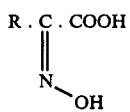
(VII)

(where R has the above-defined meaning) by reaction with a compound of general formula

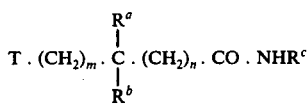
(VIII)

(wherein $R^a$, $R^b$, $R^c$, $m$ and $n$ are as hereinbefore defined and T is halogen such as chloro, bromo or iodo; sulphate; or sulphonate such as tosylate). Separation of isomers may be effected either before or after such etherification. The etherification reaction is desirably carried out in the presence of a base, e.g. potassium t-butoxide or sodium hydride, and is preferably conducted in an organic solvent, for example dimethylsulphoxide, a cyclic ether such as tetrahydrofuran or dioxan, or an N,N-disubstituted amide such as dimethylformamide. Under these conditions the configuration of the oximino group is substantially unchanged by the etherification reaction. This process is particularly useful in the preparation of acids (V) in which both $R^a$ and $R^b$ are hydrogen.

Acids (V) may also be prepared by reacting an acid of formula VII as defined above with a compound of formula

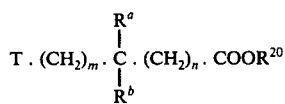
(IX)

(where $R^a$, $R^b$, T, $m$ and $n$ are as hereinbefore defined and $R^{20}$ is a carboxyl blocking group, e.g. a lower alkyl group such as methyl or ethyl) for example using conditions similar to those described above for the reaction of compounds (VII) and (VIII), and reacting the resulting compound of formula

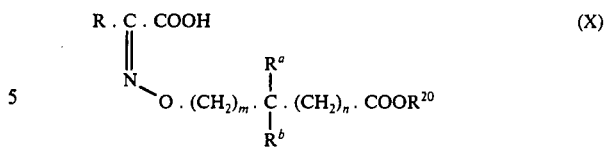
(X)

with a compound $R^c.NH_2$ (where $R^c$ is as hereinbefore defined) to yield an acid to formula V. It will be appreciated that when either $R^a$ or $R^b$ is a blocked carboxy (e.g. lower alkoxycarbonyl) group, this group may also be converted to an aminocarbonyl or N-substituted aminocarbonyl group under the reaction conditions. Separation of isomers may be effected at any appropriate stage in the reaction sequence.

Further methods of preparing acids of general formula V are as follows:

(a) Reaction of a glyoxylic acid of formula $$R.CO.COOH \quad (XI)$$

(wherein R is as defined above) with a compound of formula

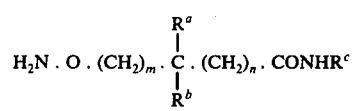
(XII)

(wherein $R^a$, $R^b$, $R^c$, $m$ and $n$ are as defined above); and (b) Reaction of a glyoxylic acid of formula XI with a compound of formula

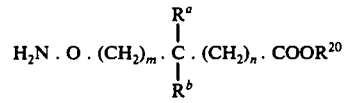
(XIII)

(wherein $R^a$, $R^b$, $R^{20}$, $m$ and $n$ are as hereinbefore defined) and reaction of the resulting compound of formula X with a compound $R^cNH_2$. Reaction of XI with XII or XIII may be followed where necessary by the separation of syn and anti isomers.

The acids of formula V may be converted to the corresponding acid halides and anhydrides by conventional methods.

Carboxyl blocking groups $R^{19}$ used in the preparation of compounds of formula I or in the preparation of necessary starting materials are desirably groups which may readily be split off at a suitable stage in the reaction sequence, conveniently as the last stage. It may, however, be convenient in some instances to employ biologically acceptable, metabolically labile carboxyl blocking groups such as acyloxymethyl groups (e.g. pivaloyloxymethyl) and retain these in the final product to give a biologically acceptable ester derivative of a compound of formula I.

Suitable carboxyl blocking groups are well known in the art, a list of representative blocked carboxyl groups being included in Belgian Pat. No. 783,449. Preferred blocked carboxyl groups include aryl lower alkoxycarbonyl groups such as p-methoxybenzyloxycarbonyl, p-nitrobenzyloxycarbonyl and diphenylmethoxycarbonyl; lower alkoxycarbonyl groups such as t-butoxycarbonyl; and lower haloalkoxycarbonyl groups such as 2,2,2-trichloroethoxycarbonyl. The carboxyl blocking group may subsequently be removed by any of the appropriate methods disclosed in the literature; thus, for example, acid or base catalysed hydrolysis is applicable in many cases, as are enzymically-catalysed hydrolyses.

The antibiotic compounds of the invention, e.g. compounds of formula I and non-toxic derivatives thereof, may be formulated for administration in any convenient way, by analogy with other antibiotics and the invention therefore includes within its scope pharmaceutical compositions comprising an antibiotic compound in accordance with the invention adapted for use in human or veterinary medicine. Such compositions may be presented for use in conventional manner with the aid of any necessary pharmaceutical carriers or excipients.

The antibiotic compounds according to the invention may be formulated for injection and may be presented in unit dose form in ampoules, or in multi-dose containers with an added preservative. The compositions may take such forms as suspensions, solutions, or emulsions in oily or aqueous vehicles and may contain formulatory agents such as suspending, stabilising and/or dispersing agents. Alternatively the active ingredient may be in powder form for reconstitution with a suitable vehicle, e.g. sterile, pyrogen-free water, before use.

The antibiotic compounds may also be presented in a form suitable for absorption by the gastro-intestinal tract, e.g. as tablets or capsules. The antibiotic compounds may also be formulated as suppositories, e.g. containing conventional suppository bases such as cocoa butter or other glyceride.

Compositions for veterinary medicine may, for example, be formulated as intramammary preparations in either long acting or quick-release bases.

The compositions may contain from 0.1% upwards, e.g. 0.1–99%, preferably from 10–60% of the active material, depending on the method of administration. When the compositions comprise dosage units, each unit will preferably contain 50–1500 mg of the active ingredient. The dosage as employed for adult human treatment will preferably range from 500 to 5000 mg per day, depending on the route and frequency of administration, although in treating Pseudomonas infections higher daily doses may be required.

The antibiotic compounds according to the invention may be administered in combination with other therapeutic agents such as antibiotics, for example penicillins, tetracyclines or other cephalosporins.

The following examples illustrate the invention. All temperatures are in ° C. The structure of the products were verified by p.m.r. and i.r. spectroscopy.

PREPARATION 1

2-Aminocarbonylmethoxyimino-2-(fur-2-yl)acetic acid (syn isomer)

To a solution of potassium t-butoxide (2.24 g) in dimethylsulphoxide (10 ml) was added a solution of 2-hydroxyimino-2-(fur-2-yl)acetic acid (syn isomer) (1.551 g) in dimethylsulphoxide (10 ml). The mixture was stirred for 30 minutes and a solution of chloroacetamide (0.935 g) in dimethylsulphoxide (10 ml) was added. The mixture was stirred for a further 2 hours, when a clear solution had formed. This solution was poured into ice-water (50 ml) and the mixture was extracted with ethyl acetate. The layers were separated and the aqueous layer was acidified with 2N hydrochloric acid and extracted with ethyl acetate. The ethyl acetate extracts were washed with brine and dried, and the solvent was evaporated. The resulting yellow oil was triturated with dichloromethane to give the title compound (0.51 g, 24%), m.p. 143°–145°; $\lambda$max (EtOH) 275nm ($\epsilon$ 14,100).

PREPARATION 2

2-(2-Aminocarbonylprop-2-yloxyimino)-2-(fur-2-yl)acetic acid (syn isomer)

2-(2-Ethoxycarbonylprop-2-yloxyimino)-2-(fur-2-yl) acetic acid (syn isomer) (2.0 g) was dissolved in concentrated aqueous ammonia (50 ml) and the solution stood at room temperature for 22 hours. Most of the ammonia was removed by evaporation and the solution was then acidified with concentrated hydrochloric acid and extracted with ether. The ether extracts were washed with brine and dried and the solvent was removed to give a white solid. Trituration with dichloromethane gave the title compound (1.37 g, 77%), m.p. 160°–162°; $\lambda$max (EtOH) 271nm ($\epsilon$ 15,100).

PREPARATION 3–19

Method A

The dipotassium salt of the 2-(aryl)-2-hydroxyiminoacetic acid (syn isomer) was generated by treating a solution of the acid in dimethylsulphoxide with 2 equivalents of potassium t-butoxide. After stirring of this solution for 10–30 minutes the appropriately substituted $\alpha$-halo-acetamide or alkyl $\alpha$-halo-acetate was added and the mixture was stirred for a further 1–2 hours and worked up as described in Preparation 1 to give the appropriate amido- or alkoxycarbonyl-substituted acid derivative.

Method B

The ethoxycarbonyl-substituted acid products of Preparations 5–8 and 18 were treated for 17–24 hours in an aqueous solution containing an excess of ammonia or methylamine and worked up with ethyl acetate or ether as described in Preparation 2 to give the corresponding amido-substituted acid derivatives shown in Preparations b 9–14 and 19.

Method C 2-(1-t-Butoxycarbonyl-1-ethoxycarbonylethoxyimino)-2-(fur-2-yl) acetic acid (syn isomer) [prepared by alkylating the dipotassium salt of 2-(fur-2-yl)-2-hydroxyiminoacetic acid (syn isomer) with ethyl t-butyl $\alpha$-bromo-$\alpha$-methylmalonate] was treated in accordance with the procedure given in Method B to yield the amido-substituted acid derivative shown in Preparation 15.

The compounds prepared by these methods are listed in Tables I and Ia and are identified with reference to the formula

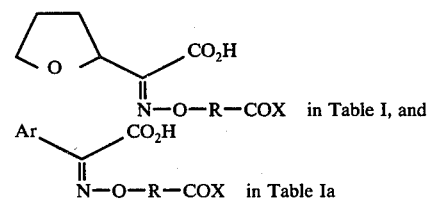

TABLE 1

| Preparation No. | R | X | Method | m.p. (° C) | $\lambda_{max, nm}$ (EtOH) | $\epsilon$ |
|---|---|---|---|---|---|---|
| 3 | \C(CH₃)₂/ | NHC(CH₃)₃ | A | 134–136 | 270.5 | 15,500 |
| 4 | \C(CH₃)₂/ | OC₂H₅ | A | 72–74 | 269.5 | 15,400 |
| 5 | \C(cyclopentyl)/ | OC₂H₅ | A | — | 271.5 | 15,600 |
| 6 | \C(cyclobutyl)/ | OC₂H₅ | A | — | — | — |
| 7 | \CHCH₃*/ | OC₂H₅ | A | 74–76 | 274.5 | 15,200 |
| 8 | \C(CH₃)(CO₂C₂H₅)/ | OC₂H₅ | A | oil | 271.5 | 14,400 |
| 9 | \C(cyclopentyl)/ | NH₂ | B | 169–171 | 271.5 | 15,700 |
| 10 | \C(cyclobutyl)/ | NH₂ | B | 176–178 | 274.5 | 14,700 |
| 11 | \CHCH₃*/ | NH₂ | B | 130–132 | 272 | 14,700 |
| 12 | \C(CH₃)(CONH₂)/ | NH₂ | B | 138–146 | 274 | 15,400 |
| 13 | \C(cyclopentyl)/ | NHCH₃ | B | 137–140 | 275 | 15,300 |
| 14 | \CHCH₃*/ | NHCH₃ | B | 134–136 | 272 | 15,200 |
| 15 | \C(CH₃*)(CO₂C(CH₃)₃)/ | NH₂ | C | 130–131 | 276 (pH 6 buffer) | 16,800 |

* Denotes (RS)-isomers

TABLE 1a

| Preparation | Ar | R | X | Method | m.p. (° C) | $\lambda_{max, nm}$ (EtOH) | $\epsilon$ |
|---|---|---|---|---|---|---|---|
| 16** | Ph | —CH₂— | NH₂ | A | 144° | 253.5 | 11,700 |
| 17 | thienyl (S) | —CH₂— | NH₂ | A | 134–138° | 287 | 10,000 |
| 18 | thienyl (S) | —C(CH₃)₂— | OC₂H₅ | A | oil | 286.5 | 9,200 |

TABLE 1a-continued

| Preparation | Ar | R | X | Method | m.p. (° C) | $\lambda_{max}$, nm (EtOH) | $\epsilon$ |
|---|---|---|---|---|---|---|---|
| 19 | (2-thienyl) | $-\underset{CH_3}{\underset{|}{C}}-CH_3$ | NH$_2$ | B | 175–176° | 287.5 | 10,400 |

**Prepared from iodoacetamide

The substituted ethyl α-bromoacetates used in Preparations 5 and 6 were made as follows:

PREPARATION 20

1-Bromo-1-ethoxycarbonylcyclopentane

A solution of 1-bromocyclopentanecarboxylic acid (5.1 g) in ethanol (40 ml) containing concentrated sulphuric acid (10 drops) was refluxed for 4 hours. The solvent was removed by evaporation and the residual oil was partitioned between ether (50 ml) and 2N sodium carbonate (30 ml).

The ether extract was washed with water (100 ml) and dried. The solvent was evaporated to give the title compound as a yellow oil (3.94 g, 68%), which was used without further purification.

Similarly was prepared:

PREPARATION 21

1-Bromo-1-ethoxycarbonylcyclobutane 63.2% Yield, used without further purification.

EXAMPLE 1

(6R, 7R)-3-Acetoxymethyl-7-[2-aminocarbonylmethoxyimino-2-(fur-2-yl)acetamido]ceph-3-em-4-carboxylic acid (syn isomer)

To a suspension of 2-aminocarbonylmethoxyimino-2-(fur-2-yl)acetic acid (syn isomer) (0.424 g) in a solution of t-butyl (6R,7R)-3-acetoxymethyl-7-aminoceph-3-em-4-carboxylate (0.656 g) in dry dichloromethane, was added dicyclohexylcarbodiimide (0.414 g). The mixture was stirred for 2 hours and filtered, and the filtrate was evaporated to dryness. The residue was dissolved in ethyl acetate (25 ml) and washed successively with 2N hydrochloric acid, aqueous sodium bicarbonate and brine. The ethyl acetate solution was dried and the solvent was removed by evaporation. The residue was dissolved in trifluoroacetic acid (20 ml) and the resulting solution was stood at room temperature for 10 minutes, whereafter the solvent was removed by evaporation. The residue was partitioned between ethyl acetate and 2N hydrochloric and the mixture was filtered and the layers were separated. The ethyl acetate layer was extracted with dilute aqueous sodium bicarbonate and the aqueous extract was acidified with 2N hydrochloric acid and extracted with ethyl acetate. The ethyl acetate extract was dried and evaporated to dryness. The, residue was dissolved in ethyl acetate (5 ml) and isopropyl ether was added to give the title compound (0.492 g, 53%); $[\alpha]_D$ +33°; $\lambda_{max}$ (EtOH) 236.5 and 275 nm ($\epsilon$ 11,000; 14,900); $\beta_{max}$ (CHBr$_3$) includes 1770(β-lactam); $\tau$(DMSO-d$_6$) includes 0.05(d, J8Hz, —CONH—), 4.11(dd, J 8 and 5Hz, C7-H) and 5.50 (=NOCH$_2$—).

EXAMPLES 2–9

The compounds listed in Table 2 were prepared by condensing t-butyl (6R,7R)-3-acetoxymethyl-7-aminoceph-3-em-4-carboxylate (1 equivalent) with the appropriate 2-[aminocarbonyl(optionally substituted methoxyimino)]-2-(fur-2-yl)acetic acid (syn isomer)(1 equivalent) with dicyclohexylcarbodiimide (1 equivalent) in dry dichloromethane (Method A) or where the components are insufficiently soluble in dichloromethane alone, in a mixture of dry dichloromethane and dry dimethylformamide (Method B). The reaction mixture was stirred at 0°–25° for 2 hours, whereafter the product was isolated by evaporation of the dichloromethane and thereafter partitioning the residue between ethyl acetate and 2N- hydrochloric acid. The organic layer so obtained was washed successively with aqueous sodium bicarbonate and brine, and was then evaporated to dryness. The residue was dissolved in trifluoracetic acid (4–20 ml /g), left at room temperature for 10 minutes, and then worked up as described in Example 1.

The compounds prepared by this method are listed in Table 2 and are identified with reference to the formula

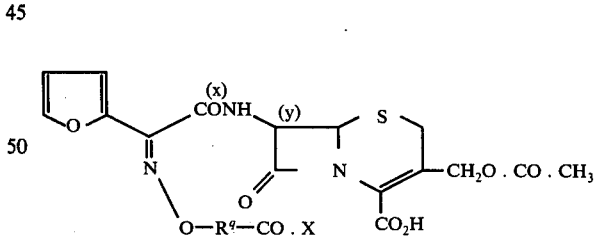

TABLE 2

| Ex. No. | R$^q$ | X | Method | $[\alpha]_D$ (DMSO) | $\lambda_{max, nm}$ (EtOH) | $\epsilon$ | β-lactam $\nu_{max, cm}^{-1**}$ | τ values for d$_6$-DMSO at 100 MHz | | |
|---|---|---|---|---|---|---|---|---|---|---|
| | | | | | | | | x | y | R$^q$ |
| 2 | \C(CH$_3$)$_2$/ | NH$_2$ | B | +54° | 272.5 | 17,300 | 1775 | 0.18 | 4.10 | 8.57 |
| 3 | \C/ (cyclopentyl) | NH$_2$ | B | +28° | 274 | 18,600 | 1780 | 0.19 | 4.10 | 7.95, 8.35 |

TABLE 2-continued

| Ex. No. | $R^q$ | X | Method | $[\alpha]_D$ (DMSO) | $\lambda_{max, nm}$ (EtOH) | $\epsilon$ | β-lactam $\nu_{max, cm}^{-1}$** | τ values for $d_6$-DMSO at 100 MHz x | y | $R^q$ |
|---|---|---|---|---|---|---|---|---|---|---|
| 4 | ⟩C⟨▱ | NH₂ | B | — | 274 | 15,300 | 1784 | 0.11 | 4.10 | 7.3 – 8.4 |
| 5 | ⟩CHCH₃* | NH₂ | B | +54° | 274.5 | 15,500 | 1781 | 0.09 | 4.11 | 5.4; 8.62 |
| 6 | ⟩C(CH₃)(CONH₂) | NH₂ | B | +22° | 274.5 | 16,600 | 1785 | 0.13 | 4.05 | 8.40 |
| 7 | ⟩C⟨◯ | NHCH₃ | B | +49° | 274 | 18,600 | 1779 | 0.23 | 4.09 | 7.95 – 8.32 |
| 8 | ⟩C(CH₃)₂ | NHC(CH₃)₃ | A | +44° | 273 | 18,300 | 1788 | 0.08 | 4.15 | 8.56 |
| 9 | ⟩CHCH₃ | NHCH₃ | B | +54.5° | 274.5 | 14,900 | 1781 | 0.15 | 4.09 | 8.60 |

*Denotes (RS)-isomers
**measured in Nujol unless otherwise stated.

EXAMPLE 10

(6R,7R)-7-[2-Aminocarbonylmethoxyimino-2-(fur-2yl)-acetamido]-3-carbamoyloxymethyl-ceph-3-em-4-carboxylic acid (syn isomer)

To a solution of diphenylmethyl (6R,7R)-7-amino-3-carbamoyloxymethylceph-3-em-4-carboxylate (1.98 g) in dichloromethane (30 ml) containing dicyclohexylcarbodiimide (0.93 g) was added, dropwise at 0°, a solution of 2-aminocarbonylmethoxyimino-2-(fur-2-yl)acetic acid (syn isomer) (0.954 g) in dimethylformamide (10 ml). Dimethylformamide (20 ml) was added and the mixture was stirred at 0° for 2 hours and filtered. Dichloromethane was removed by evaporation and the remaining solution was partitioned between ethyl acetate and N hydrochloric acid. The ethyl acetate layer was washed successively with N Na₂CO₃ and brine, and then dried. The solvent was removed by evaporation. The residue was dissolved in a mixture of trifluoroacetic acid (12 ml) and anisole (3 ml), and the resulting solution was stood at room temperature for 15 minutes. The solvent was removed by evaporation and the residue was dissolved in ethyl acetate. The solution was filtered and the volume reduced to ca. 2 ml by evaporation. Isopropyl ether (60 ml) was added to give a pink solid which was filtered off and dried in vacuo. The pink solid was partitioned between N Na₂CO₃ and ethyl acetate and the layers were separated. The aqueous layer was acidified with 2N hydrochloric acid and extracted with ethyl acetate. The ethyl acetate extract was dried and concentrated to ca. 3 ml. Isopropyl ether (80 ml) was added to give the title compound (0.33 g, 15.5%), $\lambda_{max}$ (EtOH) 274nm ($\epsilon$ 14,700); $\nu_{max}$ (Nujol) includes 1770 cm⁻¹ (β-lactam); τ(DMSO-d₆) includes 0.05(d, J 8Hz, —CONH—), 4.11(C7-H) and 5.49 (s, =NOCH₂—).

EXAMPLE 11

(6R,7R)-7-[2-(2-Aminocarbonylprop-2-yloxyimino)-2-(fur-2-yl)-acetamido]-3-carbamoyloxymethylceph-3-em-4-carboxylic acid (syn isomer)

To a solution of diphenylmethyl (6R,7R)-7-amino-3-carbamoyloxymethylceph-3-em-4-carboxylate (0.88 g) and 2-(2-aminocarbonylprop-2-yloxyimino)-2-(fur-2-yl)acetic acid (syn isomer) (0.48 g) in a mixture of dichloromethane (20 ml) and dimethylformamide (10 ml), cooled in an icebath, was added dicyclohexylcarbodiimide (0.414 g). The mixture was stirred for 2 hours and the dichloromethane removed by evaporation. The residual slurry was partitioned between ethyl acetate and 2N sodium carbonate, and the mixture was filtered. The ethyl acetate extract was washed successively with 2N-hydrochloric acid and water and was then dried. The solvent was evaporated, the residue was dissolved in anisole (5 ml) and trifluoroacetic acid (10 ml) was added to the resulting solution. This was stood at room temperature for 15 minutes and the solvent was then removed by evaporation. The residue was partitioned between N sodium carbonate and ethyl acetate. The ethyl acetate layer was washed with aqueous sodium carbonate and the combined aqueous extracts were washed with ethyl acetate:ether (1:1), acidified with 2N hydrochloric acid and extracted with ethyl acetate. The ethyl acetate extracts were dried and the solvent was removed by evaporation. The residue was dissolved in ethyl acetate (4 ml) and added dropwise to well stirred light petrol (300 ml) to give the title compound (0.52 g, 52.5%), $[\alpha]_D$ +60°; $\lambda_{max}$(EtOH) 273nm ($\epsilon$ 16,800); $\nu_{max}$ (Nujol) includes 1780 cm⁻¹ (β-lactam); τ(DMSO-d₆) includes 0.11 (d, J 8Hz, —CONH—), 4.10(C7-H) and 8.55 and 8.56 (—C(CH₃)₂—).

EXAMPLE 12

(6R, 7R)-7-[2-(1-Aminocarbonylcyclobut-1-yloxyimino)-2-(fur-2-yl)-acetamido]-3-carbamoyloxymethylceph-3-em-4-carboxylic acid (syn-isomer)

Treatment of diphenylmethyl (6R, 7R)-7-amino-3-carbamoyloxymethylceph-3-em-4-carboxylate and 2-(1-aminocarbonylcyclobut-1-yloxyimino)-2-(fur-2-yl) acetic acid with dicyclohexylcarbodiimide, and subsequent removal of the protecting group from the product, as described in Example 11, gave the title compound $\lambda_{max}$ (EtOH) 272.5 nm ($\epsilon$ 19,100), $\nu_{max}$ (Nujol) includes 1780 cm$^{-1}$ ($\beta$-lactam), $\tau$ (DMSO d6) includes 0.02 (d, J 8 Hz, —CONH—), 4,08 (C7-H), 7.2–7.9 and 7.8–8.4 (cyclobutyl).

EXAMPLE 13

(6R, 7R)-3-Acetoxymethyl-7-[2-(RS-1-aminocarbonyl-1-carboxyethoxyimino-2-(fur-2-yl)acetamido]ceph-3-em-4-carboxylic acid (syn isomer)

(a) Oxalyl chloride (0.16 ml) was added to an ice-cooled, stirred solution of 2-(1-aminocarbonyl-1-t-butoxycarbonyl ethoxyimino)-2-(fur-2-yl)acetic acid (syn isomer) (0.55g) in dichloromethane (15ml) containing triethylamine (0.26ml) and N,N-dimethylformamide (one drop). The resulting solution was stirred for 30 minutes at 0°–5° and was then concentrated under reduced pressure. The residue in acetone (25ml) was added over 30 minutes to an ice-cooled, stirred solution of (6R, 7R)-3-acetoxymethyl-7-aminoceph-3-em-4-carboxylic acid (0.46 g) and sodium bicarbonate (0.296g) in water (21 ml) and acetone (17 ml). When the addition was complete, the solution was stirred for a further 2.5 hours at ambient temperature. Acetone was removed under reduced pressure, and the aqueous residue was acidified under ether to pH 1.5 with concentrated hydrochloric acid. The acidic mixture was extracted further with ethyl acetate, and the combined extracts were washed with water, dried and concentrated to give (6R, 7R)-3-acetoxymethyl-7-[2-(RS-1-aminocarbonyl-1-t-butoxycarbonyl ethoxyimino)-2-(fur-2-yl) acetamido]-ceph-3-em-4-carboxylic acid (syn isomer) (0.955g).

(b) A solution of the product of (a) above (0.66g) in anisole (2ml) was treated with trifluoroacetic acid (5ml) at ambient temperature for 15 minutes. Excess solvent was removed under reduced pressure, and the residue was distributed between ethyl acetate and aqueous sodium bicarbonate, The aqueous phase was separated and acidified to pH 1.5 under ethyl acetate. The acidified mixture was extracted further with ethyl acetate. The combined extracts were washed, dried, and concentrated to give the title compound (0.45g), $[\alpha]_D$+29.5° (c 1.0, DMSO); $\lambda_{max}$(pH6 phosphate buffer) 274.5 nm ($\epsilon$ 16,100); $\nu_{max}$(Nujol) 1770 cm$^{-1}$ ($\beta$-lactam); $\tau$ (DMSO-d$_6$) include 0.17 (CONH), 4.11 (d,C7-H), and 8.36, 8,38 (Ca1.5 proton singlets for diastereoisomeric C—CH$_3$groups).

EXAMPLE 14

(6R, 7R)-7-[2-(1-Aminocarbonylcyclobut-1-yloxyimino)-2-(fur-2-yl)acetamido]-3-pyridiniummethylceph-3-em-4-carboxylate (syn isomer)

Pyridine (1.5 ml) and (6R, 7R)-3-acetoxymethyl-7-[2-(1-aminocarbonylcyclobut-1-yloxyimino)-2-(fur-2-yl)-acetamido]ceph-3-em-4-carboxylic acid (syn isomer) (1.39 g) were added to a solution of sodium iodide (5 g) in water (1.7 ml) at 80°. The mixture was stirred at 80° for 1 hour and was then diluted with water (35 ml). The aqueous solution was washed with ether and ethyl acetate and was then acidified to pH 1 wtih 2N sulphuric acid. The mother liquors were decanted from the deposited solid, washed with ethyl acetate (50 ml) and adjusted to pH 6 with 2N sodium hydroxide solution. The resulting solution was concentrated in vacuo and the residue was diluted with water (20 ml) and passed down a colume of XAD-2resin (150 g, 2 × 70 cm) using water as eluant. After all inorganic salts had been eluted, the eluant was changed to 20% v/v aqueous ethanol and the fractions monitored by UV-spectroscopy. Those fractions containing a pyridinium-type chromophore were combined and freezedried to yield 0.38 g of the title compound, $\lambda_{max}$ (pH 6 buffer) 261 ($\epsilon$ 19,200), 264,5 ($\epsilon$ 19,200) and 281.5 nm ($\epsilon$ 19,600); $\epsilon_{max}$ (Nujol) includes 1777 cm$^{-1}$(62 -lactam); $\tau$(D$_2$O) includes 4.05 (d,J5H, C7-H), and 7.2–8.4 (cyclolbutyl protons).

EXAMPLE 15

(6R, 7R)-7-[2-Aminocarbonylprop-2-yloxyimino)-2-(fur-2-yl)-acetamido]-3-pyridiniummethylceph-3-em-4-carboxylate (syn isomer)

(6R, 7R)-3-Acetoxymethyl-7-[2-aminocarbonylprop-2-yl-oxyimino-2-(fur-2-yl)acetamido]ceph-3-em-4-carboxylic acid (syn isomer) (3.96 g) was heated in water (5 ml) containing sodium iodide (15 g) and pyridine (4.5 ml) at 80° for 1 hour and the resulting solution was worked up as described in Example 12 to give the title compound, $\lambda_{max}$ 265 ($\epsilon$19,500) and 278 nm ($\nu$ 19,700); $\nu_{max}$ (Nujol) includes 1772cm$^{31\ 1}$ ($\beta$-lactam); $\tau$(D$_2$O) values include 4.12 (d, J 5Hz, C7-H) and 8.49 (—C(CH$_3$)$_2$—).

EXAMPLE 16

(6R, 7R)-7-[2-(2-Aminocarbonylprop-2-yloxyimino)-2-(thien-2-yl)-acetamido]-3-(5-methyl-1,3,4-thiadiazol-2-ylthiomethyl)ceph-3-em-4-carboxylic acid (syn isomer)

Treatment of diphenylmethyl 86R, 7R)-3-(5-methyl-1,3,4-thiadiazol-2-yl)-thiomethyl-7-aminoceph-3-em-4-carboxylate and 2-(2-aminocarbonylprop-2-yloxyimino)-2-(thien-2-yl)-acetic acid with dicyclohexylcarbodiimide, and subsequent removal of the protecting group from the product, as described in Example 11 gave the title compound, $[\alpha]_D^{23}$−19°, $\lambda_{max}$ (MeOH) 2 72.5 nm ($\epsilon$16,600), $\nu_{max}$ (Nujol) includes 1778 cm$^{-1}$ ($\beta$-lactam), $\tau$ (DMSO d6) includes 0.06 (d, J8 Hz, —CONH—, 4.05 (C7-H), 8.51 (prop-2-yl).

EXAMPLE 17

(6R, 7R)-7-[2-(2-Aminocarbonylmethoxyimino)-2-(thien-2-yl)-acetamido]-3-(5-methyl-1,3,4-thiadiazol-2-ylthiomethyl)-ceph-3-em-4-carboxylic acid (syn isomer)

Treatment of diphenylmethyl (6R, 7R)-3-(5-methyl-1,3,4-thiadiazol-2-yl)-thiomethyl-7-aminoceph-3-em-4-carboxylate and 2-(2-aminocarbonylmethoxyimino)-2-(thien-2-yl)-acetic acid with dicyclohexylcarbodiimide, and subsequent removal of the protecting group from the product, as described in Example 11, gave the title compound, $\lambda_{max}$ (EtOH) 273 nm ($\epsilon$ 17,000) $\nu_{max}$ (Nujol) includes 1780 cm$^{-1}$, $\tau$ (DMSO d6) includes 0.18 (—CONH—), 3.98 (C7-H), 5.40 (OCH$_2$CO), 7.20 (C—CH$_3$).

EXAMPLE 18

(6R, 7R)-7-[2-(2-Aminocarbonylmethoxyimino)-2-phenylacetamido]-3-(1-methyltetrazol-5-ylthiomethyl)-ceph-3-em-4-carboxylic acid Treatment of diphenylmethyl (6R, 7R)-3-(1-methyltetrazol-5-yl)-thiomethyl-7-aminoceph-3-em-4-carboxylate and 2-(2-aminocarbonylmethoxyimino-2-phenylacetic acid with dicyclohexylcarbodiimide, and subsequent removal of the protecting group from the product, as described in Example 11, gave the title compound as its trifluoroacetic acid salt.$\lambda_{max}$(EtOH) 259 nm ($\epsilon$ 17,200), $\nu_{max}$(Nujol) includes 1780 cm$^{-1}$($\beta$-lactam), $\tau$ (DMSO d6) include 0.00 (—CONH), 4.03 (C7-H), 5.42 (OCH$_2$CO), 6.01 (N—CH$_3$).

EXAMPLE 19

Pivaloyloxymethyl (6R, 7R)-7-[2-aminocarbonylmethoxyimino-2-(fur-2-yl)acetamido]-3-carbamoyloxymethylceph-3-em-4-carboxylate (syn isomer).

Iodomethylpivalate (1.15 g) was added to a solution of sodium (6R, 7R)-7-[2-aminocarbonylmethoxyimino-2-(fur-2-yl) acetamido]-3-carbamoyloxymethylceph-3-em-4-carboxylate (syn isomer) (1.96 g) in dimethylformamide (16 ml) and the resulting mixture was stirred in an ice-bath for 15 minutes. The mixture was diluted with ethyl acetate and washed with water. The organic layer was dried and concentrated in vacuo. The residue was chromatographed on silica gel preparative plates using ethyl acetate as eluant, isolation of the slower-running major component yielding the title compound (0.74 g, 33%), $\lambda_{max}$ (EtOH) 240 nm ($\epsilon$ 13,600); $\nu_{max}$ (Nujol) includes 1788cm$^{-1}$ ($\beta$-lactam); $\tau$ (DMSO-d$_6$) includes 0.01 (d, J 8Hz,—CONH—), 4.08 (dd, J 5 and 8 Hz, C7-H) and 5.49 (=NOCH$_2$—).

Pharmaceutical compositions according to the invention may be formulated according to the following Examples.

EXAMPLE A

Water Soluble Cephalosporin (a) Dry Powder for Injection

The sterile sodium salt of (6R, 7R)-3-acetoxymethyl-7-[2-aminocarbonylmethoxyimino-2-(fur-2-yl)acetamido]ceph-3-em-4-carboxylic acid is filled into glass vials, the claimed contents of each container being 500mg and 1.0g of the cephalosporin. Filling is carried out aseptically under a blanket of nitrogen. The vials ae closed using rubber discs or plugs held in position by aluminium sealing rings, thereby preventing gaseous exchange or ingress of microorganisms. It would be possible to reconstitute the product by dissolving in water for injections or other suitable sterile vehicle shortly before administration. If the compound is required for administration in an insufficient volume of water for injections to give complete solution, it may be necessary to mill the material before fillings.

(b) Intramammary Injection (for a lactating cow)

| Percentage Composition (w/w) | |
|---|---|
| Sodium salt of the cephalosporin used in (a) | 8.33 as sodium salt |
| Vehicle to: | 100.00 |
| Vehicle: Tween 60 | 3.00 |
| White Beeswax | 6.00 |
| Arachis Oil | 91.00 |

The three ingredients of the vehicle are heated together at 150° C for 1 hour and then cooled to room temperature with stirring. The sterile antibiotic, finely powdered, is added aseptically to this vehicle and the product refined with a high speed mixer. The preparation is filled aseptically into sterile containers such as collapsible aluminium tubes or plastic syringes. The fill weight is 3.0g, each container holding 250mg of the cephalosporin acid as sodium salt. The product would be intended for administration into the mammary gland through the teat canal.

EXAMPLE B

Sparingly Soluble Cephalosporin (betaine)-(6R, 7R)-7-[2-(1-Aminocarbonylcyclobut-1-yloxyimino)-2-(fur-2yl)acetamido]-3-pyridiniummethylceph-3-em-4-carboxylate (syn isomer) Dry Powder for Injection (suspension)

| Composition per dose (5ml) | |
|---|---|
| Cephalosporin Derivative | 1.00g |
| Lecithin | 20mg |
| Sodium Carboxymethyl Cellulose (low viscosity) | 30mg |
| Sodium Citrate (anhydrous) | 100mg |

The sodium carboxymethyl cellulose and anhydrous sodium citrate, both as fine powders, are sterilised by maintaining them at 160° C for 1 hour. The lecithin is dissolved in chloroform and sterilised by membrane filtration. The solution is then triturated aseptically with the sodium citrate. The chloroform is allowed to evaporate and the lecithin-coated sodium citrate aseptically sieved or milled. Continuing to use aseptic precautions, the sterile cephalosporin is then blended intimately with the sterile coated sodium citrate and sterile sodium carboxymethyl cellulose. The blend is filled under sterile conditions into siliconised glass vials, the latter being sealed to prevent ingress of microorganisms by using rubber discs or plugs held in position by aluminum sealing rings. A fill weight of 1.265g (10 percent overage) is used and the product would be intended for reconstitution shortly before administration with water for injections to give a final volume of 5.5ml and an injectable volume of 5.0ml.

We claim:

1. A compound selected from the group consisting of a cephalosporin antibiotic of the formula

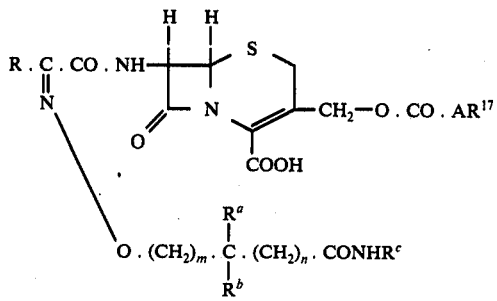

wherein R is phenyl, thienyl or furyl; $R^a$ and $R^b$ are each hydrogen, $C_{1-4}$ alkyl, $C_{2-4}$ alkenyl, $C_{3-7}$ cycloalkyl, carboxy, $C_{2-5}$ alkoxycarbonyl, aminocarbonyl, N-($C_1$-$C_4$alkyl)aminocarbonyl or cyano, or $R^a$ and $R^b$ together with the carbon atom to which they are attached form a $C_{3-7}$ cycloalkylidene or cycloalkenylidene group; $R^c$ is hydrogen or $C_{1-4}$ alkyl; m and n are each 0 or 1 such that the sum of m and n is 0 or 1; A is >O, >S or >NH; and $R^{17}$ is hydrogen or $C_{1-7}$ alkyl and a physiologically acceptable salt, metabolically labile ester pr 1-oxide thereof.

2. The compound of claim 1 which is (6R, 7R)-7-[2-aminocarbonylmethoxyimino-2-(fur-2-yl)-acetamido]-3-carbamoyloxymethyl-ceph-3-em-4-carboxylic acid (syn isomer).

3. The compound of claim 1 is (6R, 7R)-7-[2-(2-aminocarbonylprop-2-yloxyimino)-2-(fur-2-yl)acetamido]-3-carbamoyloxymethylceph-3-em-4-carboxylic acid (syn isomer).

4. The compound of claim 1 which is pivaloyloxymethyl (6R, 7R)-7-[2-aminocarbonylmethoxyimino-2-(fur-2-yl)acetamido]-3-carbamoyloxymethylceph-3-em-4-carboxylate (syn isomer).

5. The compound of claim 1 which is (6R, 7R)-7-[2-(1-aminocarbonylcyclobut-1-yloxyimino)-2-(fur-2-yl)-acetamido]-3-carbamoyloxymethyl-ceph-3-em-4-carboxylic acid (syn isomer).

6. A compound according to claim 1 wherein $R^a$ and $R^b$ together with the carbon atom to which they are attached form a cyclobutylidene, cyclopentylidene or cyclohexylidene group.

* * * * *